(12) United States Patent
Getts et al.

(10) Patent No.: US 9,670,533 B2
(45) Date of Patent: Jun. 6, 2017

(54) METHODS, REAGENTS AND KITS FOR DETECTION OF NUCLEIC ACID MOLECULES

(71) Applicant: Genisphere, LLC, Hatfield, PA (US)

(72) Inventors: Robert C. Getts, Collegeville, PA (US); James Kadushin, Gilbertsville, PA (US); Jessica Bowers, Harleysville, PA (US)

(73) Assignee: Genisphere LLC, Hatfield, PA (US)

( * ) Notice: Subject to any disclaimer, the term of this patent is extended or adjusted under 35 U.S.C. 154(b) by 680 days.

(21) Appl. No.: 14/187,806

(22) Filed: Feb. 24, 2014

(65) Prior Publication Data

US 2014/0296092 A1 Oct. 2, 2014

Related U.S. Application Data

(62) Division of application No. 12/031,165, filed on Feb. 14, 2008, now Pat. No. 8,685,899.

(60) Provisional application No. 60/901,361, filed on Feb. 14, 2007.

(51) Int. Cl.
*C40B 30/04* (2006.01)
*C12Q 1/68* (2006.01)

(52) U.S. Cl.
CPC .......... *C12Q 1/6837* (2013.01); *C12Q 1/682* (2013.01); *C40B 30/04* (2013.01)

(58) Field of Classification Search
None
See application file for complete search history.

(56) References Cited

U.S. PATENT DOCUMENTS

| | | | |
|---|---|---|---|
| 4,735,800 | A | 4/1988 | Collett et al. |
| 5,175,270 | A | 12/1992 | Nilsen et al. |
| 5,484,904 | A | 1/1996 | Nilsen et al. |
| 5,487,973 | A | 1/1996 | Nilsen et al. |
| 5,538,872 | A | 7/1996 | Bahl et al. |
| 6,046,038 | A | 4/2000 | Nilsen |
| 6,072,043 | A | 6/2000 | Nilsen |
| 6,110,687 | A | 8/2000 | Nilsen |
| 6,117,631 | A | 9/2000 | Nilsen |
| 6,168,948 | B1 | 1/2001 | Anderson et al. |
| 6,344,316 | B1 | 2/2002 | Lockhart et al. |
| 6,762,292 | B2 | 7/2004 | Nilsen |
| 2002/0051981 | A1 | 5/2002 | Getts |
| 2006/0094025 | A1 | 5/2006 | Getts et al. |
| 2006/0099619 | A1 | 5/2006 | Remacle et al. |
| 2006/0160098 | A1 | 7/2006 | Zak et al. |
| 2006/0166235 | A1 | 7/2006 | Hennessy et al. |

(Continued)

FOREIGN PATENT DOCUMENTS

| | | |
|---|---|---|
| WO | WO-00/04192 | 1/2000 |
| WO | WO-03/106637 | 12/2003 |
| WO | WO-2006/050433 | 5/2006 |

OTHER PUBLICATIONS

3DNA Array900 miRNA RT, *Genisphere*, XP002694382 Dec. 15, 2004, 14 pages.

(Continued)

*Primary Examiner* — Christian Boesen
(74) *Attorney, Agent, or Firm* — Servilla Whitney LLC

(57) ABSTRACT

Methods, reagents and kits are provided for the production and use in detection assays of labeled nucleic acid molecules wherein a labeling molecule is attached directly to the 3' end of the nucleic acid molecules.

8 Claims, 2 Drawing Sheets

(56) References Cited

U.S. PATENT DOCUMENTS

2006/0172317 A1 8/2006 Wang
2007/0161004 A1 7/2007 Brown et al.

OTHER PUBLICATIONS

ASAP miRNA Labeling Kit for 10 Labeling Reactions and 5 Arrays Catalog No. MPS545, *Perkin Elmer Life and Analytical Sciences, Inc.: Laboratory Manual* 2004, 14 pages.
FlashTag™ Biotin RNA Labeling Kit for Affymetrix® Genechip® miRNA Arrays, *Genisphere*, XP002694379 Jun. 1, 2009, 16 pages.
Allawi, Hatim T. et al., Quantitation of microRNAs Using a Modified Invader Assay, *RNA Society, Published by Cold Spring Harbor Laboratory Press* 2004, 1153-1161.
Ambros, Victor et al., MicroRNAs and Other Tiny Endogenous RNAs in C. elegans, *Current Biology*, vol. 13 May 13, 2003, 807-818.
Aravin, Alexei A. et al., The Small RNA Profile during *Drosophila melanogaster* Development, *Developmental Cell*, vol. 5 Aug. 2003, 337-350.
Babak, Tomas et al., Probing microRNAs with microarrays: Tissue specificity and functional inference, *RNA Society*, www.rnajournal.org, vol. 10, No. 11 Nov. 2004, 1813-1819.
Bartel, David P., MicroRNAs: Genomics, Biogenesis, Mechanism, and Function, *Cell*, vol. 116 Jan. 23, 2004, 281-297.
Brennecke, Julius et al., Towards a Complete Description of the microRNA Complement of Animal Genomes, *Genome Biology*, http://genomebiology.com/2003/4/9/228, vol. 4, Issue 9 Aug. 21, 2003, Art. 228.
Calin, George A. et al., Human microRNA Genes are Frequently Located at Fragile Sites and Genomic Regions Involved in Cancers, *PNAS USA*, www.pnas.org/cgi/doi/10.1073101, vol. 101, No. 9, Mar. 2, 2004, 2999-3004.
Calin, George A. et al., MicroRNA Profiling Reveals Distinct Signatures in B Cell Chronic Lymphocytic Leukemias, *PNAS USA*, www/pnas.org/cgi/doi/10.1073/pnas.0404432101, vol. 101, No. 32 Aug. 10, 2004, 11755-11760.
Caminade, Anne-Marie et al., Uses of Dendrimers for DNA Microarrays, *Sensors*, vol. 6, ISSN: 1424-8220, XP002694383 Aug. 24, 2006, 901-914.
Carrington, James C. et al., Role of MicroRNAs in Plant and Animal Development, *Science*, www.sciencemag.org, vol. 301 Jul. 18, 2003, 336-338.
Enos, Joellyn M. et al., MicroRNA Labeling Methods Directly Influence the Accuracy of Expression Profiling Detection, *BioTechniques*, vol. 42, No. 3 2007, 378-381.
Goff, Loyal A. et al., Rational Probe Optimization and Enhanced Detection Strategy for MicroRNAs Using Microarrays, *RNA Biology*, vol. 2, No. 3, XP002694380 Jul. 2005, 93-100.
Grad, Yonatan et al., Computational and Experimental Identification of C. elegans microRNAs, *Molecular Cell*, vol. 11 May 2003, 1253-1263.
Grenier, Jennifer K. et al., Direct Labeling and Microarray Analysis of microRNA Expression Profiles, *Mirus Bio Corporation* 2004.
Griffith-Jones, Sam, The microRNA Registry, *Nucleic Acids Research*, vol. 32, Database Issue Oxford University Press 2004, D109-D111.
Iannone, Marie A. et al., Multiplexed Single Nucleotide Polymorphism Genotyping by Oligonucleotide Ligation and Flow Cytometry, *Cytometry*, vol. 39 2000, 131-140.
Jin, Peng et al., Biochemical and genetic interaction between the fragile X mental retardation protein and the microRNA pathway, *Nature Neuroscience*, vol. 7, No. 2 Feb. 2004, 113-117.
Krichevsky, Anna M. et al., A microRNA Array Reveals Extensive Regulation of microRNAs During Brain Development, *RNA*, vol. 9 2003, 1274-1281.
Lagos-Quintana, Mariana et al., Identification of Novel Genes Coding for Small Expressed RNAs, *Science*, www.sciencemag.org, vol. 294 Oct. 26, 2001, 853-857.

Lai, Eric C. et al., Computational Identification of *Drosophila* microRNA Genes, *Genome Biology* http://genomebilogy.com/2003/4/7/R42, vol. 4, Issue 7 2003, R42.
Lau, Nelson C. et al., An Abundant Class of Tine RNAs With Probable Regulatory Roles in Caenorhadbitis elegans, *Science*, www.sciencemag.org, vol. 294 Oct. 26, 2001, 858-862.
Lee, Rosalind C. et al., An Extensive Class of Small RNAs in Caenorhabditis elegans, *Science*, www.sciencemag.org, vol. 294 Oct. 26, 2001, 862-864.
Lee, Yoontae et al., MicroRNA Maturation: Stepwise Processing and Subcellular Localization, *The EMBO Journal*, vol. 21, No. 17 2002, 4663-4670.
Lim, Lee P. et al., The microRNAs of Caenorhabditis elegans, *Genes & Development*, vol. 17, www.genesdev.org Feb. 25, 2013, 991-1008.
Lim, Lee P. et al., Vertebrate MicroRNA Genes, *Science*, www.sciencemag.org, vol. 299 Mar. 7, 2013, 1540.
Liu, Chang-Gong et al., An oligonucleotide microchip for genome-wide microRNA profiling in human and mouse tissues, *PNAS USA*, www.pnas.org/cgi/doi/10.1073/pnas.0403293101, vol. 101, No. 26 Jun. 29, 2004, 9740-9744.
Maroney, Patricia A. et al., Direct detection of small RNAs using splinted ligation, *Nature Protocols*, vol. 3, No. 2 2008, 279-287.
Mattie, Michael D. et al., Optimized high-throughput microRNA expression profiling provides novel biomarker assessment of clinical prostate and breast cancer biopsies, *Molecular Cancer*, vol. 5, ISSN: 1476-4598, XP008125351, Biomed Central, London, GB Jun. 19, 2006, 24-37.
Miska, Eric A. et al., Microarray analysis of microRNA expression in the developing mammalian brain, *Genome Biology*, http://genomebiology.com/2004/5/9/R68, vol. 5, Issue 9 2004, R68:1-13.
Mora, Johanna R. et al., *BioTechniques*, vol. 41, No. 4, XP002695559 Oct. 2006, 1-5; Supplementary Figure S1.
Mora, Johanna R. et al., Enzymatic microRNA detection in microtiter plates with DNA dendrimers, *BioTechniques*, vol. 41, No. 4, ISSN: 0736-6205, XP002694381 Oct. 2006, 1-5.
Mourelatos, Zissimos et al., miRNPs: a novel class of ribonucleoproteins containing numerous microRNAs, *Genes & Development*, vol. 16, www.genesdev.org. Feb. 6, 2002, 720-728.
Nilsen, Thor W. et al., Dendritic Nucleic Acid Structures, *J. Theor. Biol.* vol. 187 No. 2 Jul. 21, 1997, 273-284.
Schembri, Frank et al., MicroRNAs as modulators of smoking-induced gene expression changes in human airway epithelium, *PNAS USA*, vol. 106, No. 7, ISSN: 1091-6490, XP055058305 Feb. 17, 2009, 2319-2324.
Schmittgen, Thomas D. et al., A High-Throughput Method to Monitor the Expression of microRNA Precursors, *Nucleic Acids Research*, vol. 32, No. 4 Feb. 25, 2004, E43:1-10.
Sempere, Lorenzo F. et al., Expression profiling of mammalian microRNAs uncovers a subset of brain-expressed microRNAs with possible roles in murine and human neuronal differentiation, *Genome Biology*, http://genomebiology.com/2004/5/3/R13, vol. 5, Issue 3 Feb. 16, 2004, R13.
Sioud, Mouldy et al., Profiling microRNA expression using sensitive cDNA proves and filter arrays, *BioTechniques*, vol. 37, No. 4 2004, 574-580.
Stears, Robin L. et al., A novel, sensitive detection system for high-density microarrays using dendrimer technology, *Physiological Genomics*, vol. 3, American Physiological Society, ISSN: 1094-8341, XP002292926 Sep. 1, 2000, 93-99.
Wang, Hui et al., Direct and sensitive miRNA profiling from low-input total RNA, *RNA*, vol. 13 2007, 151-159.
Wang, Jia-Fu et al., Identification of 20 microRNAs from Oryza sativa, *Nucleic Acids Res.*, vol. 32, No. 5 Mar. 12, 2004, 1688-1695.
Watt, Mary-Anne V. et al., Direct Chemical Labeling of Microarray Samples with Label IT® μArray™ Biotin Labeling Kit: A Versatile, Sensitive Improvement on Traditional Enzymatic Labeling Procedures, *Mirus Bio Corporation*, www.mirusbio.com Jul. 2004, 3 pages.
Final Office Action in U.S. Appl. No. 12/625,657, dated Jan. 30, 2014, 7 pages.

METHODS, REAGENTS AND KITS FOR DETECTION OF NUCLEIC ACID MOLECULES

CROSS-REFERENCE TO RELATED APPLICATIONS

This application is a divisional of copending U.S. patent application Ser. No. 12/031,165, filed Feb. 14, 2008, which claims the benefit of U.S. Provisional Application 60/901,361, filed on Feb. 14, 2007, the contents of which are hereby incorporated by reference in their entirety.

CROSS-REFERENCE TO SEQUENCE LISTING

The Sequence Listing submitted in the present application on Jun. 10, 2014, identified as "DSC0023-00US Sequence Listing_ST25.txt" (created Apr. 7, 2008, 949 bytes) is hereby incorporated by reference in its entirety.

BACKGROUND OF THE INVENTION

Recently, a class of small non-coding RNAs, termed microRNAs (miRNAs), has been identified that function in post-transcriptional regulation of gene expression in plants and amimals (Carrington and Ambrose, Science 301:336 (2003)). Originally identified in C. elegans, miRNAs act by basepairing to complementary sites in the 3' untranslated region (UTR) or coding sequences of their target mRNAs and repressing their translation (Wang et al., Nucleic. Acids Res. 32:1688 (2004)).

While mature miRNAs are only ~22 nucleotides (nt) in length, they originate from hairpin regions of ~70 mer precursor (pre-miRNA) sequences through the action of Dicer complex (Lee et al., EMBO J. 21:4663 (2002)). The mature miRNA is then incorporated into the miRNP, the ribonucleoprotein complex that mediates miRNA's effects on gene regulation (Mourelatos et al., Genes Dev. 16:720 (2002)).

Bioinformatics studies predict that there are ~100 miR-NAs encoded in the worm and fly genomes, and ~250 miRNAs encoded in the vertebrate genomes (Lai et al., Genome Biol. 4:R42 (2003); Lim et al., Genes Dev. 17:991 (2003); Lim et al., Science 299:1540 (2003)). This accounts for ~0.5-1% of the number of predicted protein-coding genes for each genome, underlining the importance of miRNAs as a class of regulatory gene products (Brennecke and Cohen, Genome Biol. 4:228 (2003)).

miRNAs have been implicated in a variety of biological processes, including flower and leaf development in plants, larval development in worms, apoptosis and fat metabolism in flies, and hematopoietic differentiation and neuronal development in mammals (Bartel, Cell 116:281 (2004)). In addition, many miRNA genes map to chromosomal regions in humans associated with cancer (e.g., fragile sites, breakpoints, regions of loss of heterozygosity, regions of amplification) (Calin et al., Proc. Natl. Acad. Sci. USA 101:2999 (2004)). Various miRNAs have also been shown to interact with the fragile X mental retardation protein (FMRP) in vivo (Jin et al., Nat. Neurosci. 7:113 (2004)), suggesting a role for these tiny RNAs in human health and disease.

Because different cell types and disease states are associated with expression of certain miRNAs, it is important to obtain both temporal and spatial expression profiles for miRNAs. Northern hybridization has been used to determine the expression levels of miRNAs (see, e.g., Sempere et al., Genome Biol. 5:R13 (2004); Aravin et al., Dev. Cell 5:337 (2003); Grad et al., Mol. Cell 11:1253 (2003); Lim et al., Genes & Dev. 17:991 (2003)), but this method is too labor intensive for high-throughput analyses. PCR-based methods have been used to monitor the expression of miRNAs, but these methods either require the use of costly gene-specific primers (see, e.g., Schmittgen et al., Nucleic Acids Res. 32:e43 (2004)) or inefficient blunt-end ligations to attach primer-binding linkers to the miRNA molecules (see, e.g., Miska et al., Genome Biol. 5:R68 (2004); Grad et al., Mol. Cell 11:1253 (2003); Lim et al., Genes & Dev. 17:991 (2003)). In addition, PCR can introduce significant biases into the population of amplified target miRNA molecules.

High-throughput microarrays have recently been developed to identify expression patterns for miRNAs in a variety of tissue and cell types (see, e.g., Babak et al., RNA 10:1813 (2004); Calin et al., Proc. Natl. Acad. Sci. USA 101:11755 (2004); Liu et al., Proc. Natl. Acad. Sci. USA 101:9740 (2004); Miska et al., Genome Biol. 5:R68 (2004); Sioud and Røsok, BioTechniques 37:574 (2004); Krichevsky et al., RNA 9:1274 (2003)). The use of microarrays has several advantages for detection of miRNA expression, including the ability to determine expression of multiple genes in the same sample at a single time point, a need for only small amounts of RNA, and the potential to simultaneously identify the expression of both precursor and mature miRNA molecules.

However, since mature miRNAs are only ~22 nt in length and present in very limited quantities in any given tissue, these small RNAs present challenges for microarray labeling and detection (Sioud and Røsok, BioTechniques 37:574 (2004)). For example, covalent attachment of fluorophores can be used to directly label miRNA molecules for use in microarray analyses (see, e.g., Babak et al., RNA 10:1813 (2004); MICROMAX ASAP miRNA Chemical Labeling Kit, Perkin Elmer, Waltham, Mass.; Label IT® µArray Labeling Kit, Minis Bio Corp., Madison, Wis.), but this method lacks the sensitivity to detect rare target miRNA molecules. Direct labeling can also result in intermolecular quenching of the randomly incorporated fluorophores, resulting in further decreased sensitivity. Random primed-reverse transcription of miRNA molecules has been used to produce labeled cDNA molecules for use in microarray analyses (see, e.g., Sioud and Røsok, BioTechniques 37:574 (2004); Liu et al., Proc. Natl. Acad. Sci. USA 101:9740 (2004)), but this method does not yield an accurate representation of the original full-length miRNA population.

New methods of labeling have been developed that have significantly improved both the accuracy and sensitivity of miRNA analysis (see, e.g., copending U.S. patent application Ser. No. 10/979,052, published as U.S. Patent Publication No. 2006/0094025). However, these methods utilize indirect label attachment and require multiple hybridization steps in order to develop the signal in the assay. Further, these methods are encumbered with large capture reagent molecules that require an independent hybridization step in order to improve the binding kinetics. While providing good results, these methods do not allow for easy adaptation to high through-put analysis and require significantly more time to achieve the desired results. As a result, there is an immediate need for rapid, sensitive and efficient methods for labeling and detection of miRNA molecules for use in microarray and high through-put analyses.

SUMMARY OF THE INVENTION

Applicants have invented methods for the labeling of target miRNA molecules, wherein a nucleic acid labeling molecule is attached directly to the 3' end of the miRNA molecules. Applicants have discovered that quenching can be reduced and signal intensity enhanced without the need for PCR through the use of an optimized nucleic acid labeling molecule, resulting in improved methods and reagents for miRNA analyses, particularly high-throughput analyses. The optimized nucleic acid labeling molecule is preferably a multi-labeled polymeric scaffold to which a plurality of label molecules capable of emitting or producing a detectable signal is attached. The multi-labeled polymeric scaffold can be any polymer to which label molecules can be attached, such as, e.g., proteins, peptides, carbohydrates, polysaccharides, lipids, fatty acids, nucleic acids, etc. In preferred embodiments, the multi-labeled polymeric scaffold comprises a small DNA dendrimer comprising 20-1000 bases, more preferably, 300-750 bases of nucleic acid and containing one ligatable end and 10-15 label molecules capable of emitting or producing a detectable signal. The ligatable end has a 5' phosphate that can be ligated to the 3' end of a miRNA molecule. The nucleic acid labeling molecule is sufficiently small in size such that it allows for the rapid, efficient hybridization to the miRNA molecule on a variety of detection platforms, such as microarrays and bead-based assays.

Accordingly, one aspect of the present invention is directed to a multi-labeled polymeric scaffold to which a plurality of label molecules capable of emitting or producing a detectable signal is attached, wherein the multi-labeled polymeric scaffold comprises an oligonucleotide tail comprising a 5' phosphate group capable of hybridization bonding to a nucleic acid sequence. In preferred embodiments, the multi-labeled polymeric scaffold has a total molecular weight of about 50 to about 350 kDa. In some embodiments, the label molecules comprise one or more fluorophore moieties. In other embodiments, the label molecules comprise one or more biotin moieties.

In preferred embodiments, the nucleic acid sequence to which the extension sequence is capable of bonding is a bridging oligonucleotide that also is capable of hybridizing to a nucleic acid molecule separate and distinct from the polymeric scaffold. Together, the polymeric scaffold and bridging oligonucleotide constitute a system for labeling a nucleic acid molecule. Preferably, the nucleic acid molecule separate and distinct from the polymeric scaffold is a RNA molecule, more preferably a noncoding or miRNA molecule. The presence of the 5' phosphate group allows the polymeric scaffold to be ligated to the 3' end of the RNA molecule.

In a preferred embodiment, the multi-labeled polymeric scaffold is a linear dendritic polynucleotide composition having a plurality of single stranded regions to which one or more labeled oligonucleotides can be hybridized; said linear dendritic polynucleotide composition being comprised of first, second and third polynucleotide monomers bonded together by hybridization in a 5'-3' orientation; each polynucleotide monomer, prior to being hybridization bonded to one another, having first, second and third single stranded hybridization regions; and in said linear dendritic polynucleotide composition the third single stranded hybridization region of the first polynucleotide monomer being hybridization bonded to the first single stranded hybridization region of the second polynucleotide monomer, and the third single stranded hybridization region of the second polynucleotide monomer being hybridization bonded to the first single stranded hybridization region of the third polynucleotide monomer, wherein the first single strand region of the first polynucleotide monomer is capable of hybridization bonding to a nucleic acid sequence, and wherein the second single stranded hybridization regions within said linear dendritic polynucleotide composition are hybridization bonded to one or more labeled oligonucleotides comprising one or more label molecules.

Another aspect of the present invention is directed to a method for producing a labeled target miRNA molecule comprising:
a) providing a single stranded miRNA molecule having 5' and 3' ends;
b) attaching an oligonucleotide tail onto the 3' end of the single stranded miRNA molecule;
c) providing a partially double stranded nucleic acid sequence having a sense strand and antisense strand, wherein the sense strand comprises a nucleic acid labeling molecule comprising one or more label molecules capable of emitting or producing a detectable signal at its 3' end and the antisense strand comprises a single stranded 3' overhang comprising a sequence complementary to the oligonucleotide tail;
d) annealing the partially double stranded nucleic acid sequence to the oligonucleotide tail by complementary base pairing with the 3' overhang sequence; and
e) ligating the 5' end of the sense strand of the partially double stranded nucleic acid sequence to the 3' end of the oligonucleotide tail, thereby attaching the nucleic acid labeling molecule comprising one or more label molecules capable of emitting or producing a detectable signal to the 3' end of the miRNA molecule, thereby producing a labeled target miRNA molecule.

In some embodiments, the miRNA molecule is provided in a source of total RNA, while in other embodiments, the miRNA molecule is provided in a source of RNA enriched in low molecular weight RNA molecules. The oligonucleotide tail is preferably a polydA tail attached using poly(A) polymerase. Ligation is preferably performed using T4 DNA ligase. In preferred embodiments, the partially double stranded nucleic acid sequence is comprised of the multi-labeled polymeric scaffold and bridging oligonucleotide described, more preferably the linear dendritic polynucleotide composition described above.

Another aspect of the present invention is directed to a method for the detection of a miRNA antisense probe on a solid support comprising:
a) contacting a solid support having thereon an antisense probe comprising the complementary nucleotide sequence of a miRNA molecule with a labeled target miRNA molecule produced by a method comprising:
i) providing a single stranded miRNA molecule having 5' and 3' ends;
ii) attaching an oligonucleotide tail onto the 3' end of the single stranded miRNA molecule;
iii) providing a partially double stranded nucleic acid sequence having a sense strand and antisense strand, wherein the sense strand comprises a nucleic acid labeling molecule comprising one or more labels capable of emitting or producing a detectable signal at its 3' end and the antisense strand comprises a single stranded 3' overhang comprising a sequence complementary to the oligonucleotide tail;
iv) annealing the partially double stranded nucleic acid sequence to the oligonucleotide tail by complementary base pairing with the 3' overhang sequence; and
v) ligating the 5' end of the sense strand of the partially double stranded nucleic acid sequence to the 3' end of the oligonucleotide tail, thereby attaching the nucleic acid labeling molecule comprising one or more labels capable of emitting or producing a detectable signal to the 3' end of the miRNA molecule, thereby producing a labeled target miRNA molecule; and b) incubating the solid support and the labeled target miRNA molecule for a time and at a temperature sufficient to enable the labeled target miRNA molecule to hybridize to the miRNA antisense probe;

c) washing the solid support to remove unhybridized labeled target mRNA; and d) detecting the signal from the hybridized labeled target miRNA molecule, thereby detecting a miRNA antisense probe on a solid support.

In some embodiments, the solid support is a planar solid support, such as a microarray or microtiter plate, while in other embodiments, the solid support is a bead. The miRNA probe can be specific for both mature or pre-miRNA sequences or for pre-miRNA sequences alone.

Another aspect of the present invention is directed to a kit for the production of labeled target miRNA molecules for use in miRNA analyses comprising: a partially double stranded nucleic acid sequence having a sense strand and antisense strand, wherein the sense strand comprises a nucleic acid labeling molecule comprising one or more labels capable of emitting or producing a detectable signal and the antisense strand comprises a single stranded 3' overhang comprising a sequence complementary to an oligonucleotide tail; and instructional materials for producing a labeled target miRNA molecule using the partially double stranded nucleic acid sequence.

In some embodiments, the kit also comprises at least one enzyme for attaching an oligonucleotide tail onto the 3' end of a target miRNA molecule, wherein the oligonucleotide tail is complementary to the single stranded 3' overhang sequence of the partially double stranded nucleic acid sequence; and at least one enzyme for attaching the 5' end of the sense strand of the partially double stranded nucleic acid sequence to the 3' end of the target miRNA molecules. In other embodiments, a plurality of nucleic acid labeling molecules capable of emitting or producing different detectable signals are provided to allow dual or multiple color assays to be performed. In preferred embodiments, the partially double stranded nucleic acid sequence is comprised of the multi-labeled polymeric scaffold and bridging oligonucleotide described above. In more preferred embodiments, the multi-labeled polymeric scaffold is the linear dendritic polynucleotide composition described above.

DETAILED DESCRIPTION

Figure 1:
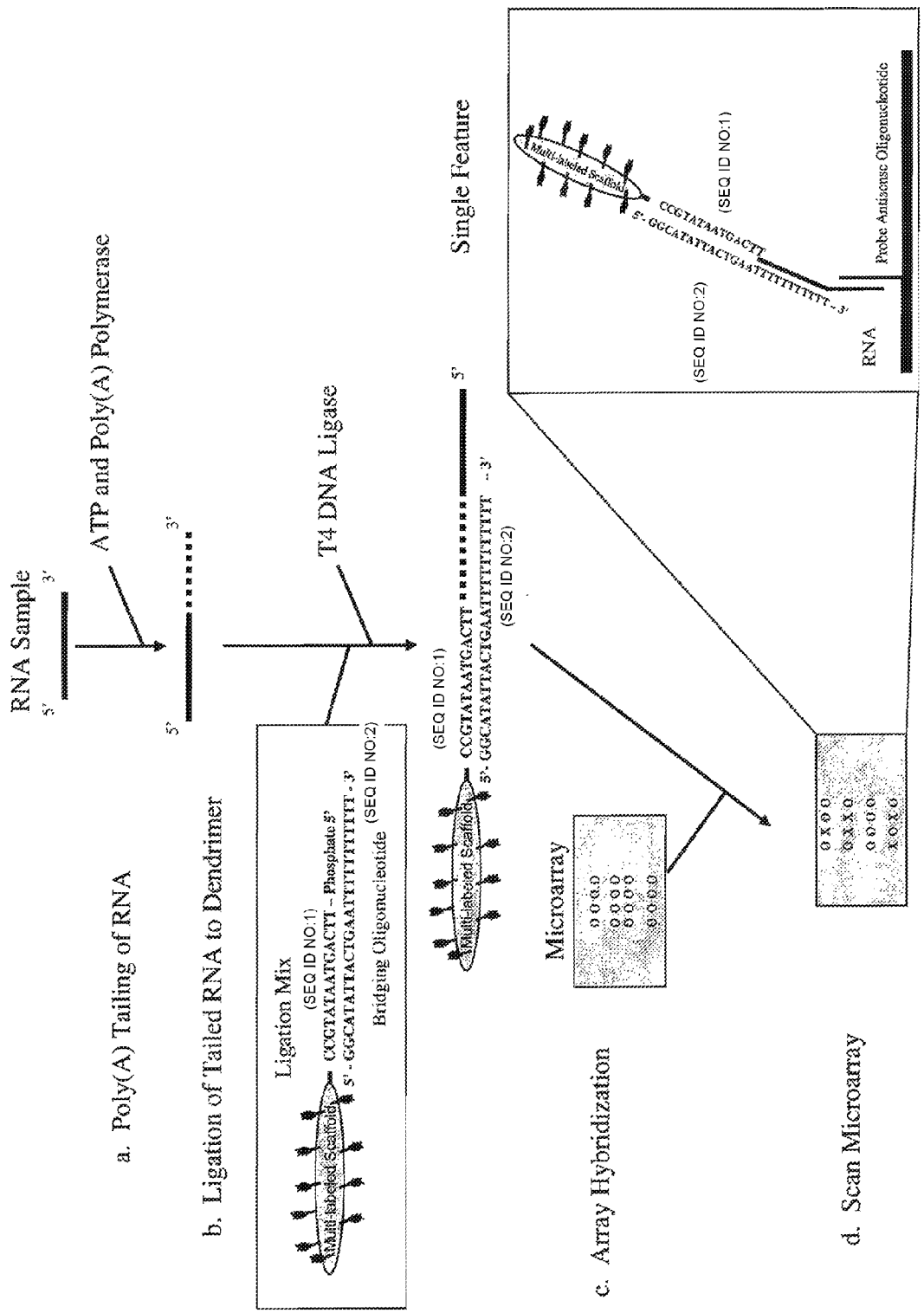
FIG. 1a-d together depict labeling of a target miRNA molecule and the detection of miRNA probes according to the methods of the present invention.

The present invention relates to nucleic acid molecules, methods and kits for use in RNA microarray analyses. The terms "RNA molecule", "miRNA molecule" "mRNA molecule", "DNA molecule", "cDNA molecule", and "nucleic acid molecule" are each intended to cover a single molecule, a plurality of molecules of a single species, and a plurality of molecules of different species. The term "miRNA molecule" is also intended to cover both mature and pre-miRNA molecules. Consistent with microarray terminology, "target miRNA" refers to a miRNA or complementary cDNA sequence to be labeled, while "miRNA probe" refers to an unlabeled sense or antisense miRNA sequence attached directly to a solid support. The term "nucleic acid labeling molecule" refers to any non-native nucleotide sequence capable of being ligated to the 3' end of a miRNA molecule, such as a DNA dendrimer, and comprising one or more label molecules capable of emitting or producing a detectable signal.

The methods of the present invention comprise attaching a nucleic acid labeling molecule comprising a label capable of emitting or producing a detectable signal onto the 3' end of at least one miRNA molecule. The resulting labeled miRNA molecule(s) are then used to detect miRNA probes attached to a solid support, allowing miRNA expression profiles to be obtained. By using appropriately labeled target molecules and appropriately designed probes, the both mature and pre-miRNA expression profiles can be determined.

The methods of the present invention are distinct over currently available technologies that directly label target miRNA molecules by covalent attachment of fluorophores or that random prime and reverse transcribe target miRNA molecules to produce labeled cDNA molecules, both of which lack the sensitivity necessary for detecting rare target miRNA molecules following hybridization to miRNA probes. The methods of the present invention are also distinct over PCR-based labeling technologies, which can introduce amplification bias into the population of labeled target molecules.

The methods of the present invention utilize routine techniques in the field of molecular biology. Basic texts disclosing general molecular biology methods include Sambrook et al., *Molecular Cloning, A Laboratory Manual* (3d ed. 2001) and Ausubel et al., *Current Protocols in Molecular Biology* (1994).

The methods of the present invention utilize sources of RNA molecules. Preferably, the sources are enriched for miRNA molecules. Although reference is made throughout to "miRNA" and "enrichment," it should be understood that the methods disclosed herein can be used to label any nucleic acid molecule with a 3' end, whether enriched or otherwise, including RNA molecules with modified 3' ends, such as those found in plants and bacteria. The methods of the present invention may also be extended to labeling DNA molecules having available 3' ends in combination with enzymes that will synthesize a polymeric tail on the 3' ends in the presence a deoxyribonucleotide. One example of an enzyme capable of synthesizing a polymeric tail in the presence of a deoxyribonucleotide is terminal deoxynucleotide transferase (TdT). Numerous methods and commercial kits are available for the enrichment of miRNA molecules from total RNA. Examples include the miRvana™ miRNA Isolation Kit (Ambion, Austin, Tex.), PureLink™ miRNA Isolation kit (Invitrogen, Carlsbad, Calif.), mirPremier™ microRNA isolation kit (Sigma-Aldrich, St. Louis, Mo.) and miRNeasy Mini kit (Qiagen, Valencia, Calif.), purification on denaturing PAGE gels (see, e.g., Miska et al., *Genome Biol.* 5:R68 (2004)), centrifugation with appropriately sized molecular weight cutoff filters (e.g., Microcon® YM filter devices, Millipore, Billerica, Mass.), and sodium acetate/ethanol precipitation (see, e.g., Wang et al., *Nucleic Acids Res.* 32:1688 (2004)).

The miRNA may be obtained from any tissue or cell source that contains miRNA, including virion, plant, and animal sources found in any biological or environmental sample. Preferably, the source is animal tissue, more preferably mammalian tissue, most preferably human tissue. The RNA may also be purified from clinical FFPE samples using an RNA extraction kit, such as, e.g., the RecoverAll™ Total Nucleic Acid Isolation kit (Ambion, Austin Tex.).

The RNA may be subjected to an amplification process. Examples of RNA amplification kits include, but are not limited to, the SenseAMP RNA amplification kit (Genisphere, Hatfield, Pa.), MessageAmp™ RNA Amplification kit (Ambion, Austin, Tex.), Ovation™ RNA Amplification system (NuGen Technologies, San Carlos, Calif.), and the like.

With reference to FIG. 1, a single stranded oligonucleotide tail is attached to the 3' end of single stranded miRNA molecules (see FIG. 1a). The oligonucleotide tail can be incorporated by any means that attaches nucleotides to single stranded RNA. Preferably, the oligonucleotide tail is attached to the single stranded cDNA using poly(A) polymerase (PAP), or other suitable enzyme, in a suitable buffer in the presence of appropriate nucleotides. Preferably, the oligonucleotide tail is a homopolymeric nucleotide tail (i.e., polyA, polyG, polyC, or polyT). Preferably, the oligonucleotide tail is a polyA tail, generally ranging from about 3 to greater than 500 nucleotides in length, preferably from about 20 to about 100 nucleotides in length. When using PAP, a preferred buffer is Tris-HCl, pH 8.0 (or other suitable buffer), containing both magnesium and manganese ions. For example, the buffer may comprise 1 to 100 mM Tris-HCl, pH 8.0, 1 to 20 mM $MgCl_2$ and 1 to 20 mM $MnCl_2$, as well as 0.01 to 20 mM ATP. The tailing reaction typically takes place at 37° C. for 5 to 60 minutes.

To produce labeled target miRNA molecules, a partially double stranded deoxynucleic acid sequence containing a sense strand comprising a nucleic acid labeling molecule comprising one or more labels capable of emitting or producing a detectable signal at its 3' end is attached to the 3' oligonucleotide tail by ligation (see FIG. 1b). This is facilitated through complementary base pairing between the 3' oligonucleotide tail and an overhang sequence at the 3' end of the antisense strand of the partially double stranded deoxynucleic acid sequence that contains a sequence of deoxynucleotides complementary to the oligonucleotide tail. For example, if the oligonucleotide tail is a polyA tail, the 3' overhang of the partially double stranded deoxynucleic acid sequence will contain a sequence of deoxythymidines at its 3' end, generally ranging from about 3 to greater than 50 nucleotides in length, preferably from about 10 to about 30 nucleotides in length. The particular nucleotide sequence of the 3' overhang sequence does not have to be perfectly (i.e., 100%) complementary to the particular nucleotide sequence of the 3' oligonucleotide tail, nor does the length of the 3' overhang sequence need to be exactly equal to the length of the 3' oligonucleotide tail, for the sequences to be considered complementary to each other. Those of skill in the art will recognize that all that is required is that there be sufficient complementarity between the two sequences so that the 3' overhang can anneal to the 3' oligonucleotide tail, thus properly positioning the capture sequence at the 3' end of the miRNA molecule.

Once properly positioned, the nucleic acid labeling molecule is attached to the 3' oligonucleotide tail by ligation. Such overhang or "staggered" ligation reactions are more efficient and can be performed at higher temperatures than blunt-end ligation reactions. In addition, the use of an oligodeoxynucleotide tail allows for ligation of deoxynucleic acid labeling molecule DNA to the DNA tail, which is more efficient than ligation of DNA directly to miRNA. Any DNA ligase can be used in the ligation reaction. Preferably, the DNA ligase is T4 DNA ligase. When using T4 DNA ligase, a preferred buffer is a ¹/₁₀ dilution of 10× Ligation Buffer (660 mM Tris-HCl, pH 7.5, 50 mM MgCl, 10 mM DTT, 10 mM ATP) supplied by Roche Applied Science, Indianapolis, Ind. The reaction is preferably terminated by the addition of EDTA.

The nucleic acid labeling molecule used in the ligation reaction is preferably a multi-labeled polymeric scaffold to which a plurality of label molecules capable of emitting or producing a detectable signal is attached. The scaffold also comprises an oligonucleotide extension sequence comprising a 5' phosphate group for ligation to the 3' tailed miRNA molecules (see FIG. 1b). The multi-labeled polymeric scaffold can be any polymer to which label molecules can be attached, such as, e.g., proteins, peptides, carbohydrates, polysaccharides, lipids, fatty acids, nucleic acids, etc. The total molecular weight of the multi-labeled polymeric scaffold is preferably about 50 to about 350 kDa. The polymeric scaffold preferably comprises about 2-100 label molecules, which are spaced apart such that quenching is reduced or eliminated and/or access to large detection molecules (e.g., streptavidin) is allowed. One of skill in the art can determine the appropriate spacing of the label molecules based on available literature. For example, U.S. Pat. Nos. 6,762,292, 6,072,043, and 6,046,038 describe a process for determining optimal spacing for attachment of fluorescent label molecules to a nucleic acid scaffold. Generally, spacing of the label molecules at least 10 nt apart in a nucleic acid scaffold is sufficient. Spacing in other types of scaffolds can be determined accordingly.

Figure 2:
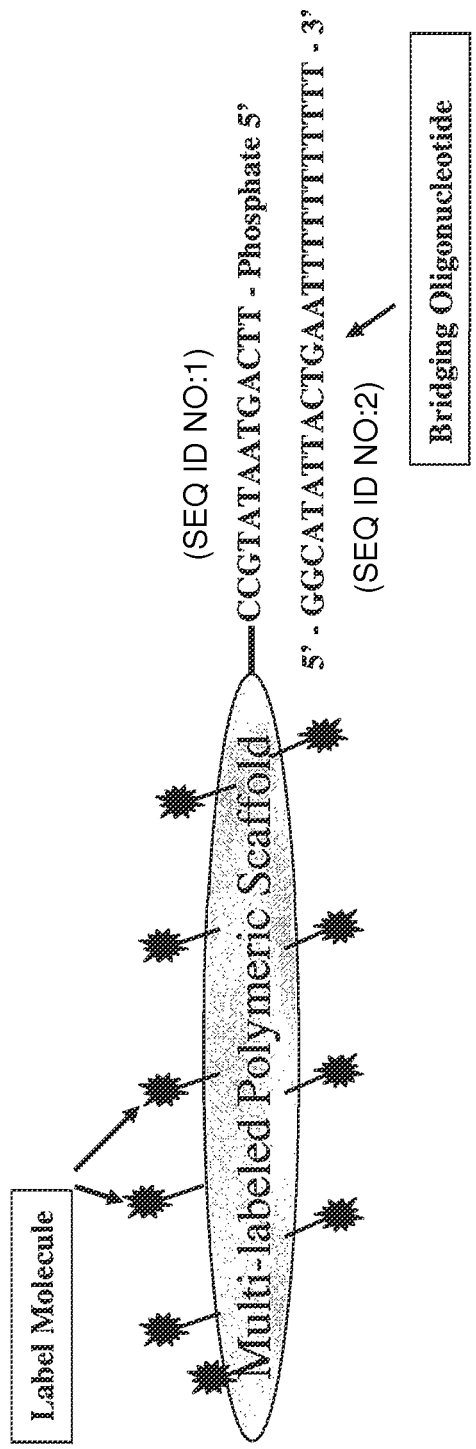
FIG. 2 depicts a preferred nucleic acid labeling molecule of the present invention.

FIG. 2 depicts a preferred multi-labeled polymeric scaffold of the present invention. The multi-labeled polymeric scaffold comprises an oligonucleotide extension sequence with a 5' phosphate group capable of hybridization bonding to a nucleic acid sequence. In this embodiment, the nucleic acid sequence is the bridging oligonucleotide shown in FIG. 2, the 5' portion of which is complementary to the oligonucleotide tail of the polymeric scaffold, and the 3' portion of which is complementary to the 3' oligonucleotide tail of the miRNA molecules. Together, the polymeric scaffold and bridging oligonucleotide constitute a system for labeling the miRNA molecules. The 5' phosphate group on the oligonucleotide tail allows the polymeric scaffold to be ligated to the miRNA molecules. The bridging oligonucleotide is typically in molar excess, preferably in about 1.8-2.6-fold molar excess, to that of the oligonucleotide tail of the polymeric scaffold during the ligation reaction. The hybridized bridging oligonucleotide/polymeric scaffold oligonucleotide tail together form the partially double stranded deoxynucleic acid sequence described above, thereby constituting a system for labeling the miRNA molecules. Again, it should be understood that the sequences shown in FIG. 2 are merely exemplary, and any sequences capable of hybridization can be used.

In preferred embodiments, the multi-labeled polymeric scaffold is a small linear dendritic polynucleotide composition comprising 20-1000 bases, more preferably, 300-750 bases of nucleic acid and containing one ligatable end and 10-15 label molecules capable of emitting or producing a detectable signal. As discussed above, the ligatable end has a 5' phosphate that can be ligated to the tailed miRNA molecules. In some embodiments, the linear dendritic polynucleotide composition is a small 3DNA™ Dendrimer Capture Reagent (Genisphere Inc., Hatfield, Pa.). Dendrimers are highly branched nucleic acid molecules that contain two types of single stranded hybridization "arms" on their surface for the attachment of a label molecule and a capture sequence. Because a single dendrimer may have multiples of arms of each type, the signal obtained upon hybridization is greatly enhanced. Signal enhancement using dendritic reagents is described in Nilsen et al., *J. Theor. Biol.* 187:273 (1997); Stears et al., *Physiol. Genomics* 3:93 (2000); U.S. Pat. Nos. 5,175,270, 5,484,904, 5,487,973, 6,072,043, 6,110,687, and 6,117,631; and U.S. Patent Publication No. 2002/0051981. The use of optimally designed dendrimers allows the label molecules to be placed such that quenching is reduced or eliminated. Furthermore, the signal in the labeling molecule can be amplified or enhanced without bias-introducing amplification of the target nucleic acid molecules themselves.

The linear dendritic polynucleotide composition can comprise first, second and third polynucleotide monomers bonded together by hybridization in a 5'-3' orientation, each polynucleotide monomer, prior to being hybridization bonded to one another, having first, second and third single stranded hybridization regions. The third single stranded hybridization region of the first polynucleotide monomer is hybridization bonded to the first single stranded hybridization region of the second polynucleotide monomer, and the third single stranded hybridization region of the second polynucleotide monomer is hybridization bonded to the first single stranded hybridization region of the third polynucleotide monomer. The first single stranded region of the first polynucleotide monomer of the linear dendritic polynucleotide composition is designed for hybridization binding to a nucleic acid sequence. When used in the labeling methods described herein, the nucleic acid sequence is the bridging oligonucleotide sequence shown in FIG. 2 used to attach the multi-labeled polymeric scaffold to the 3' oligonucleotide-tailed miRNA molecule.

Each of the second single stranded hybridization regions within each of the polynucleotide monomer used to assemble the linear dendritic polynucleotide composition is designed for hybridization bonding to one or more labeled oligonucleotides. The labeled oligonucleotides contain one or more label molecules. Preferably, the third single stranded hybridization region of the third polynucleotide monomer is also hybridization bonded to or more labeled oligonucleotides. The labeled linear dendritic polynucleotide composition is preferably cross-linked following assembly using e.g., psoralen chemistry.

The label molecule(s) on the nucleic acid labeling molecule can be any molecule capable of emitting or producing a detectable signal. Such molecules include those that directly emit or produce a detectable signal, such as radioactive molecules, fluorescent molecules, and chemiluminescent molecules, as well as enzymes used in colorimetric assays, such as horseradish peroxidase, alkaline phosphatase, and β-galactosidase. Such molecules also include those that do not directly produce a detectable signal but which bind in systems that do, such as biotin/streptavidin and antigen/antibody. Preferably, the signal-producing molecule is one that directly emits or produces a detectable signal, more preferably a fluorophore, most preferably a Cy3 or Cy5 dye (GE Healthcare, Piscataway, N.J.), an Oyster®-550 or Oyster®-650 dye (Denovo Biolabels, Münster, Germany), or other suitable dye, such as Alexa Fluor™ 555 or 647 dyes (Molecular Probes, Eugene, Oreg.). The use of label molecules to prepare labeled oligonucleotides is well known in the art.

The labeled miRNA molecules are then contacted with a solid support containing miRNA probes (see FIG. 1c). As used herein, "solid support" is intended to include any solid support containing nucleic acid probes, including slides, chips, membranes, beads, and microtiter plates. Methods for attaching miRNA probes to solid supports are well known to those of skill in the art (see, e.g., Babak et al., RNA 10:1813 (2004); Calin et al., *Proc. Natl. Acad. Sci. USA* 101:11755 (2004); Liu et al., *Proc. Natl. Acad. Sci. USA* 101:9740 (2004); Miska et al., *Genome Biol.* 5:R68 (2004); Sioud and Røsok, *BioTechniques* 37:574 (2004); Krichevsky et al., *RNA* 9:1274 (2003)). Alternatively, miRNA microarrays, both in planar and bead form, can be obtained commercially from, e.g., Invitrogen, Carlsbad, Calif. (NCode™ miRNA Microarray), Exiqon, Woburn, Mass. (miRCURY™ miRNA Array), CombiMatrix, Mukilteo, Wash. (miRNA CustomArray™), and Luminex, Austin, Tex. (FlexmiR™ miRNA Panel). The labeled miRNA molecules can also be used in enzyme-linked oligosorbent assays (ELOSAs).

In the case of labeled target miRNA molecules, the solid support will contain antisense miRNA probes. The probes can be designed for detection of both mature and pre-miRNA sequences, or the probes can be specific for pre-miRNA sequences. Comparison can give profiles for both the pre- and mature sequences. miRNA probes can be designed using known miRNA and pre-miRNA sequences publicly available from, e.g., The miRBase Sequence Database (http://microrna.sanger.ac.uk/sequences, The Wellcome Trust Sanger Institute, Wellcome Trust Genome Campus, Hinxton, UK (Griffiths-Jones et al., *Nucleic Acids. Res.* 34:D140 (2006). Novel miRNA sequences can also be used to design miRNA probes and can be identified using computational methods (see, e.g., Ambros et al., *Curr. Biol.* 13:807 (2003); Grad et al., *Mol. Cell* 11; 1253 (2003); Lai et al., *Genome Biol.* 4:R42 (2003); Lim et al., *Genes & Dev.* 17:991 (2003); Lim et al., *Science* 299:1540 (2003)) or miRNA cloning strategies (see, e.g., Wang et al., Nucleic Acids Res. 32:1688 (2004); Lagos-Quintana et al., *Science* 294:853 (2001); Lau et al., *Science* 294:858 (2001); Lee et al., *Science* 294:862 (2001)) well known to those skilled in the art.

The solid support and the labeled miRNA molecules are incubated in a hybridization buffer for a time and at a temperature sufficient to enable the labeled miRNA molecules to hybridize to the miRNA probes. Suitable array-based hybridization buffers include 2× SDS-based buffer (2×SSC, 4×Denhardt's solution, 1% SDS, 0.5 M sodium Phosphate, 2 mM EDTA, pH 8.0) and 2× Enhanced Hybridization Buffer (ExpressHyb™, BD Biosciences Clontech, Palo Alto, Calif.) diluted to 75% with nuclease free water. Suitable bead-based assay buffers include 4-4.5 M TMAC, 5-15% deionized formamide, 0.1-2% BSA, 0.25-1 mg/ml salmon sperm DNA.

Preferably, the solid support and the capture sequence-tagged nucleic acid molecules are incubated for about 0.5-72 hours, preferably 18-24 hours, at about 25-65°, preferably 45-65° C. Excess unhybridized labeled miRNA molecules can be removed by washing in prewarmed 2×SSC, 0.2% SDS wash buffer for 15 min at 25-60° C., preferably at 50-55° C., 2×SSC for 10-15 minutes at room temperature, and 0.2×SSC for 10-15 minutes at room temperature. The solid support is then analyzed, typically by scanning (see FIG. 1d). Microarray-based assays may be analyzed using suitable instruments, such as, e.g., a GenePix® 4000B microarray scanner with GenePix® Pro 3.0 software (Molecular Devices, Sunnyvale, Calif.) or a ScanArray™ 5000 (PerkinElmer, Waltham, Mass.). Bead-based assays may be analyzed using instrumentation and software provided by Luminex Corporation (Austin, Tex.) and similar equipment familiar to one of skill in the art.

The methods and reagents of the present invention can be conveniently packaged in kit form. Such kits can be used in various research and diagnostic applications. For example, methods and kits of the present invention can be used to facilitate a comparative analysis of expression of one or more miRNAs in different cells or tissues, different subpopulations of the same cells or tissues, different physiological states of the same cells or tissue, different developmental stages of the same cells or tissue, or different cell populations of the same tissue. Such analyses can reveal statistically significant differences in the levels of miRNA expression, which, depending on the cells or tissues analyzed, can then be used to facilitate diagnosis of various disease states, prognosis of disease progression, and identification of targets for disease treatment.

A wide variety of kits may be prepared according to the present invention. For example, a kit for the production of labeled target miRNA molecules may include a partially double stranded nucleic acid sequence having a sense strand and antisense strand, wherein the sense strand comprises a nucleic acid labeling molecule comprising one or more labels capable of emitting or producing a detectable signal and the antisense strand comprises a single stranded 3' overhang comprising a sequence complementary to an oligonucleotide tail; and instructional materials for producing labeled target miRNA molecules using the partially double stranded nucleic acid sequence. In preferred embodiments, the partially double stranded nucleic acid sequence is comprised of the multi-labeled polymeric scaffold and bridging oligonucleotide described above. In other preferred embodiments, the multi-labeled polymeric scaffold is the linear dendritic polynucleotide composition described above.

While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

The kits may also include one or more of the following components or reagents for production of the labeled miRNA molecules of the present invention: an RNase inhibitor; an enzyme for attaching an oligonucleotide tail onto single stranded RNA molecules (e.g., poly(A) polymerase); an enzyme for attaching an oligonucleotide tail onto single stranded DNA molecules (e.g., TdT); a reverse transcriptase; and an enzyme for attaching the partially double stranded nucleic acid sequence to the oligonucleotide tail (e.g., T4 DNA ligase). The kits may further include components and reagents and instructional materials for use of the labeled miRNA in miRNA assays, including hybridization and wash solutions, incubation containers, cover slips, and various signal-detecting, signal-producing, signal-enhancing, and signal-preserving reagents. Additionally, the kits may include buffers, nucleotides, salts, RNase-free water, containers, vials, reaction tubes, and the like compatible with the production and use of the labeled miRNA molecules of the present invention. The components and reagents may be provided in numbered containers with suitable storage media.

Specific embodiments according to the methods of the present invention will now be described in the following examples. The examples are illustrative only, and are not intended to limit the remainder of the disclosure in any way.

EXAMPLES

Example 1

Labeling of miRNA Molecules in Total RNA and Hybridization to Antisense miRNA Probes Preparation of a Linear Dendritic Polynucleotide Nucleic Acid Labeling Molecule A trimeric linear dendritic polynucleotide nucleic acid labeling molecule was prepared as described above. The labeling molecule had a molecular weight of 165 kDa, contained 15 fluorophore moieties at intervals of 10-15 nt and was cross-linked following assembly using trioxsalen in the presence of UV-A. The labeling molecule contained the 5'-phosphorylated oligonucleotide tail shown in FIG. 2 (5'-TTC AGT AAT ATG CC-3'; SEQ ID NO:1). The UV-irradiated formulation was purified using Microcon® YM-30 microconcentrators, as per the vendor's (Millipore, Billerica, Mass.) instructions.

Preparation of Ligation Mix Containing the Linear Dendritic Polynucleotide Nucleic Acid Labeling Molecule Forty-two µl of the purified labeling molecule (2,380 ng/µl) was combined with 12.3 µl of the bridging oligonucleotide (904 ng/µl) shown in FIG. 2 (5'-GGC ATA TTA CTG AAT TTT TTT TTT T-3'; SEQ ID NO:2) and 35 µl of 10× ligation buffer (660 mM Tris-HCl, pH 7.5, 50 mM MgCl, 10 mM DTT, 10 mM ATP; Roche Applied Science, Indianapolis, Ind.) in a final volume of 210 µl. The bridging oligonucleotide was designed for hybridization bonding to both the 5'-phosphorylated oligonucleotide tail shown in FIG. 2 and the 3' poly(A) tailed miRNA molecules described below, allowing the labeling molecule and the tailed miRNA molecules to be ligated together. The mixture was heated to 60° C. for 10 minutes in a 0.30 L water bath prepared in a 1 liter beaker. The beaker containing the ligation mix was then allowed to cool to room temperature. One hundred-forty µl of 10× ligation buffer was added and the tube mixed by vortexing. The mixture was then stored at −20° C. until use.

Tailing of miRNA Molecules

One and one/half µg rat brain total RNA and 1.5 µg rat liver total RNA (Ambion, Austin, Tex.) were separately brought to 10 µl with nuclease-free water. The total RNA was poly(A) tailed by adding 1.5 µl 10× reaction buffer (50 mM Tris-HCl, pH 8.0, 10 mM $MgCl_2$), 1.5 µl 25 mM $MnCl_2$, 1 µl 0.02 mM ATP and 1 µl poly(A) polymerase (5 U/µl) and heating at 37° C. for 15 minutes.

Ligation of miRNA

The poly(A) tailed RNA molecules were ligated by adding 4 µL of the ligation mix and 2 µl T4 DNA ligase (2 U/µl) and incubating at room temperature for 30 minutes. Reactions were stopped by adding 2.5 µl Stop Solution (0.25 M EDTA). The rat brain RNA was ligated to dendrimer molecules containing Oyster®-550 label molecules, and the rat lung RNA was ligated to dendrimer molecules containing Oyster®-650 label molecules.

Labeled miRNA Microarray Hybridization

Prior to preparing microarray hybridization mixtures, 2× Enhanced Hybridization Buffer (ExpressHyb™ buffer (BD Biosciences Clontech, Palo Alto, Calif.) diluted to 75% with nuclease-free water) was thawed and resuspended. The labeled RNA molecules were combined with 5 ul 10% BSA and 2× Enhanced Hybridization Buffer to a final concentration of 1×. The hybridization mixture was applied to a NCode™ microarray (Invitrogen, Carlsbad, Calif.), covered with a glass coverslip, and incubated overnight at 52° C. For single color assays, only one labeled miRNA population is included in the chosen hybridization mixture, with the remaining volume made up with nuclease free water.

The coverslip was removed by washing the microarray in 2×SSC, 0.2% SDS wash buffer prewarmed to 52° C. The microarray was sequentially washed in prewarmed 2×SSC, 0.2% SDS wash buffer for 15 minutes at 52° C., 2×SSC for 10-15 minutes at room temperature, and 0.2×SSC for 10-15 minutes at room temperature. The microarray was transferred to a dry 50 mL centrifuge tube, orienting the slide so that any adhesive bar code or label was down in the tube. The tube containing the microarray was immediately centrifuged without the tube cap at 800-1000 RPM to dry the microarray. The microarray was removed from the tube, taking care not to touch the microarray surface. The array was scanned using a GenePix® 4000B microarray scanner with GenePix® Pro 3.0 software (Molecular Devices, Sunnyvale, Calif.), thereby producing an expression profile of the miRNA sequences in the original samples. The brain and liver profiles were compared to establish a differential profile for various miRNAs. miR122 was observed to be present predominantly in the liver and miR 124a and miR9 predominantly in brain. miR16 and miRlet7a-f, as well as other miRNAs, were expressed in both brain and liver but demonstrated a tissue specific profile.

Example 2

Labeling of miRNA Molecules in Enriched RNA and Hybridization to Antisense miRNA Probes The procedures of Example 1 were followed, except that the rat brain and rat liver total RNA were enriched for low molecular weight RNAs prior to microarray hybridization. One and one-half µg of rat brain and rat liver total RNA were separately diluted to 100 µl with 10 mM Tris, pH 8.0, heated to 80° C. for 3 minutes, and cooled on ice. For each RNA sample, a Microcon® YM-100 microconcentrator (Millipore, Billerica, Mass.) was pre-wet by adding 50 µl 10 mM Tris, pH 8.0 and centrifuging for 3 minutes at 13,000 RPM. The columns were placed into new collection tubes and each 100 µl sample was added and centrifuged for 7 minutes at 13,000 RPM. Each flow-through containing low molecular weight RNA molecules (~95 µl) were concentrated with a Microcon® YM-3 microconcentrator (Millipore, Billerica, Mass.) by centrifuging for 30 minutes at 13,000 RPM. Five µl of 10 mM Tris-HCl, pH 8.0 was then added to each sample reservoir and gently mixed by tapping the side of the column Each sample reservoir was then placed upside down in a new collection tube and centrifuged for 3 minutes at 13,000 RPM to collect the concentrated enriched RNA (~5-10 µl recovered). Each enriched RNA sample was then brought to 10 µl with nuclease-free water.

The enriched RNA molecules were poly(A) tailed, ligated, and hybridized to a NCode™ microarray as above. Following hybridization, the array was washed and scanned as above, thereby producing an expression profile of the miRNA sequences in the original samples. When the data from Example 1 (total RNA log 2 (liver/brain)) and Example 2 (enriched RNA log 2 (liver/brain)) were compared, a Pearson correlation of 0.933 was observed.

Example 3

ELOSA

Plate Coating
A CoStar® (Corning, Lowell, Mass.) microtiter plate was coated by adding 100 µl of 1 µg/mL human miR122 antisense DNA oligonucleotide (5'-CAA ACA CCA TTG TCA CAC TCC A-3'; SEQ ID NO:3) in 1×PBS to each well. The plate was covered with a microplate press-on sealer (PerkinElmer, Waltham, Mass.) and incubated overnight at room temperature. The plate was then washed 2 times with 1×PBS, 0.05% Tween-20, and blotted dry.
Plate Blocking and miRNA Labeling
Two-hundred µl 4% BSA in 1×PBS was added to each well. The plate was covered and incubated for 1-2 hours at room temperature. During the plate blocking incubation time, miRNA molecules in total and enriched RNA were labeled. Low molecular weight RNA was enriched from 1 µg, 0.75 µg, 0.5 µg, and 0.25 µg of rat liver total RNA (Ambion, Austin, Tex.) using Microcon® YM-100 microconcentrators (Millipore, Billerica, Mass.) followed by concentration with Microcon® YM-3 microconcentrators (Millipore, Billerica, Mass.) as described in Example 2 above. The enriched RNA samples, as well as 1 µg, 0.75 µg, 0.5 µg and 0.25 µg of Rat liver total RNA were poly(A) tailed as described in Example 1 above. The tailed RNA molecules were ligated by adding 4 µl of a ligation mix and 2 µl T4 DNA ligase (2 U/µl) and incubating at room temperature for 30 minutes. The ligation mix was similar to the ligation mix in Example 1 except that the linear dendritic polynucleotide nucleic acid labeling molecule contained biotin moieties rather than fluorophore moieties. Reactions were stopped by adding 2.5 µl Stop Solution (0.25 M EDTA) to generate 23.5 µl of biotinylated RNA. After blocking was complete, the plate was washed 2 times with 1×PBS, 0.05% Tween-20 and blotted dry.
Sample Hybridization
Nineteen µl TMAC Solution (4.5 M TMAC, Sigma-Aldrich, St. Louis, Mo.), 75 mM Tris, pH 8, 0.15% sarkosyl (Sigma-Aldrich, St. Louis, Mo.), 6 mM EDTA (Ambion, Austin, Tex.)), 26 µl deionized formamide (EMD, Gibbstown, N.J.), 5 µl 10% BSA, and 1.5 µl nuclease-free water were added to each 23.5 µl biotinylated RNA sample for a final volume of 75 µl. Each sample was gently mixed, centrifuged, and applied to a coated blocked well. The samples were hybridized in the plate for 3-4 hours at room temperature. Following hybridization, the plate was first washed 2 times with 2×SSC, 0.2% SDS wash buffer prewarmed to 52° C., then washed 2 times with 2×SSC at room temperature, and then washed 2 times with 0.2×SSC at room temperature.
Streptavidin-HRP Hybridization
Streptavidin-HRP (SA-HRP, R&D Systems, Minneapolis, Minn.) was diluted in 4% BSA (Equitech-Bio, Kerrville, Tex.) in 1×PBS according to manufacturer recommendations. Fifty µl of diluted SA-HRP was added to each well and the plate incubated for 1 hour at room temperature with gentle shaking. The plate was then washed 2-4 times with 1×PBS, 0.05% Tween-20 and blotted dry.
Signal Development
One-hundred µl TMB Substrate (Pierce, Rockford, Ill.) was added to each well and the plate was incubated at room temperature for 1 to 15 minutes. One-hundred µl BioSource™ Stop Buffer (Invitrogen, Carlsbad, Calif.) was added to each well. Absorbance was read at 450 nm on a Victor$^3$ Multilabel Plate Reader (PerkinElmer, Waltham, Mass.). For both the enriched and total RNA, a linear relationship was observed between input RNA and observed signal, correlation coefficients equal to 0.985 and 0.973, respectively. The limit of detection of miR122 was determined to be less than 0.25 µg of total RNA either as enriched miRNA or total RNA.

Example 4

Luminex Bead Detection of miRNA Molecules

Total RNA samples from rat brain and liver (Ambion, Austin, Tex.) were poly(A) tailed and ligated with a biotinylated dendritic polynucleotide nucleic acid labeling molecule as described above in Example 3. Various Luminex brand carboxylated microbead preparations (Luminex, Austin, Tex.), containing varying quantities of two fluorescent dyes enabling the discrimination of one bead type from another via the ratio of the two fluorescent dyes, were covalently bound with various aminated 22mer antisense miRNA probes (IDT technologies) representing selected mature rat miRNA sequences (miRBase Sequence Database; http://microrna.sanger.ac.uk/sequences) using Luminex procedures. For a multiplex detection assay designed to simultaneous detect multiple miRNA specificities, 17 µl of the ligated RNA samples were added to multiples of various Luminex bead types in 33 µl of buffer comprising 10% formamide, 4.5 M TMAC, 0.1% BSA and 25 ng/µl salmon sperm DNA. The bead-RNA mixtures were incubated overnight in 500 µl polypropylene tubes at 47° C. with horizontal agitation at 300 RPM. The beads were transferred to a filter microplate and washed via vacuum filtration with 2×SSC, 20% formamide pre-warmed to 56° C., followed by washes at room temperature with 2×SSC, 0.2×SSC and 1×PBS. One-hundred µl of a streptavidin-phycoerythrin conjugate (Invitrogen, Carlsbad, Calif.) in 1×PBS (2 ng/µl) was added to each mixture of beads and incubated at 37° C. for 30 minutes with agitation at 300 RPM. The beads were washed three times with 1×PBS, resuspended in 125 µl 1×PBS and analyzed on the Luminex 100 IS system according to the manufacturer's recommendations. Mean fluorescent intensity (MFI) values for specific miRNA probes 2× over background values indicated specific detection of miRNA molecules in the ligated RNA preparations. The brain and liver miRNA profiles were compared to those observed on the miRNA arrays in Examples 1 and 2. Similar liver/brain profiles were observed between platforms for all miRNAs tested on the Luminex platform.

Example 5

Kit for Direct Labeling of Target miRNA Molecules for Hybridization to Antisense miRNA Probes A kit for the production and microarray hybridization of labeled target miRNA molecules was assembled with the following components:
Oyster®-550 and 650 Ligation Mixes (250 ng/µl linear dendritic polynucleotide composition and 31.7 ng/µl bridging oligonucleotide) (Genisphere, Hatfield, Pa.);
10× Reaction Buffer (50 mM Tris-HCl, pH 8.0, 10 mM $MgCl_2$);
$MnCl_2$ (25 mM);
ATP Mix (10 mM);
Poly(A) Polymerase (5 U/µl);
2× SDS-Based Hybridization Buffer (2×SSC, 4×Denhardt's solution, 1% SDS, 0.5 M sodium phosphate, 2 mM EDTA, pH 8.0);
2× Enhanced Hybridization Buffer (ExpressHyb™ buffer (BD Biosciences Clontech, Palo Alto, Calif.) prediluted to 75% with nuclease-free water);
T4 DNA Ligase (2 U/µl); and
Nuclease-Free Water.

The components were placed in numbered vials and placed in a container with a printed instruction manual for the production and microarray hybridization of labeled target miRNA molecules using the kit components.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

We claim:

1. A method for detecting an antisense probe on a solid support comprising:
 a) contacting a solid support having thereon an antisense probe comprising the complementary nucleotide sequence of a target nucleic acid molecule with a labeled target nucleic acid molecule comprising a linear dendritic polynucleotide, the linear dendritic polynucleotide comprising an oligonucleotide extension sequence having a 5' phosphate group, and first, second and third polynucleotide monomers bonded together by hybridization in a 5'-3' orientation, each polynucleotide monomer, prior to being hybridization bonded to one another, having first, second and third single stranded hybridization regions; the third single stranded hybridization region of the first polynucleotide monomer being hybridization bonded to the first single stranded hybridization region of the second polynucleotide monomer, and the third single stranded hybridization region of the second polynucleotide monomer being hybridization bonded to the first single stranded hybridization region of the third polynucleotide monomer, and the first single stranded region of the first polynucleotide monomer being hybridization bonded to a bridging oligonucleotide,
 wherein the second single stranded hybridization regions of the linear dendritic polynucleotide are hybridization bonded to one or more labeled oligonucleotides comprising one or more label molecules,
 wherein the bridging oligonucleotide is hybridization bonded to the target nucleic acid molecule and the oligonucleotide extension sequence,
 wherein the labeled target nucleic acid molecule is produced by a method comprising: a) providing a single stranded target nucleic acid molecule having 5' and 3' ends; b) attaching an oligonucleotide tail onto the 3' end of the single stranded target nucleic acid molecule; c) annealing the first single stranded region of the first polynucleotide monomer of the linear dendritic polynucleotide to the oligonucleotide tail by complementary base pairing; and d) ligating a 5' end of the linear dendritic polynucleotide to the 3' end of the oligonucleotide tail, thereby attaching the linear dendritic polynucleotide to the 3' end of the single stranded nucleic acid molecule to produce the labeled target nucleic acid molecule,
 wherein the linear dendritic polynucleotide has a total molecular weight of about 50 to about 350 kDa;
 b) incubating the solid support and the labeled target nucleic acid molecule for a time and at a temperature sufficient to enable the labeled target nucleic acid molecule to hybridize to the antisense probe;
 c) washing the solid support to remove unhybridized labeled target nucleic acid molecule; and
 d) detecting the signal from the hybridized labeled target nucleic acid molecule, thereby detecting the antisense probe on the solid support.

2. The method of claim 1, wherein the bridging oligonucleotide is hybridization bonded to a poly(A) tail of a target RNA molecule.

3. The method of claim 1, wherein the labeled target nucleic acid molecule is a labeled RNA molecule.

4. The method of claim 3, wherein the labeled RNA molecule is a labeled miRNA molecule.

5. The method of claim 1, wherein the solid support is a planar solid support or a bead.

6. The method of claim 1, wherein the labeled target nucleic acid molecule is a labeled DNA molecule.

7. The method of claim 1, wherein the linear dendritic polynucleotide comprises 10-15 label molecules.

8. The method of claim 1, wherein the linear dendritic polynucleotide comprises a labeling molecule selected from the group consisting of radioactive molecules, fluorescent molecules and chemiluminescent molecules, and enzymes used in colorimetric assays.

* * * * *

SEQUENCE LISTING

<160> NUMBER OF SEQ ID NOS: 3

<210> SEQ ID NO 1
<211> LENGTH: 14
<212> TYPE: DNA
<213> ORGANISM: Artificial Sequence
<220> FEATURE:
<223> OTHER INFORMATION: 5' Oligonucleotide Tail
<220> FEATURE:
<221> NAME/KEY: misc_feature
<222> LOCATION: (1)..(1)
<223> OTHER INFORMATION: 5' Phosphorylated

<400> SEQUENCE: 1
ttcagtaata tgcc                                                    14

<210> SEQ ID NO 2
<211> LENGTH: 25
<212> TYPE: DNA

```
<213> ORGANISM: Artificial Sequence
<220> FEATURE:
<223> OTHER INFORMATION: Bridging Oligonucleotide

<400> SEQUENCE: 2
ggcatattac tgaatttttt ttttt                                           25

<210> SEQ ID NO 3
<211> LENGTH: 21
<212> TYPE: DNA
<213> ORGANISM: Artificial Sequence
<220> FEATURE:
<223> OTHER INFORMATION: Human miR122 Antisense DNA Oligonucleotide

<400> SEQUENCE: 3
caaacaccat tgtcacactc c                                               21
```